(12) United States Patent
Larkin et al.

(10) Patent No.: US 9,109,972 B2
(45) Date of Patent: Aug. 18, 2015

(54) DIRECT FIELD ACOUSTIC TESTING SYSTEM AND METHOD

(76) Inventors: Paul Alan Larkin, Mt. Airy, MD (US); Robert Turk Goldstein, Crownsville, MD (US); Marcos A. Underwood, Cupertino, CA (US)

(*) Notice: Subject to any disclaimer, the term of this patent is extended or adjusted under 35 U.S.C. 154(b) by 841 days.

(21) Appl. No.: 13/117,870

(22) Filed: May 27, 2011

(65) Prior Publication Data

US 2012/0300579 A1   Nov. 29, 2012

(51) Int. Cl.
*G01N 29/04*   (2006.01)
*G01M 7/00*   (2006.01)

(52) U.S. Cl.
CPC *G01M 7/00* (2013.01); *G01N 29/04* (2013.01)

(58) Field of Classification Search
CPC ................................. G01M 7/00; G01N 29/04
USPC .................................................... 73/584, 662
See application file for complete search history.

(56) References Cited

U.S. PATENT DOCUMENTS

| | | |
|---|---|---|
| 4,989,158 A | 1/1991 | Sloane |
| 5,138,884 A | 8/1992 | Bonavia |
| 5,299,459 A | 4/1994 | Underwood |
| 5,638,004 A | 6/1997 | Combs et al. |
| 6,668,650 B1 | 12/2003 | Lafleur et al. |
| 2004/0024750 A1 | 2/2004 | Ulyanov et al. |

OTHER PUBLICATIONS

Larkin et al., "Recent Developments in Direct Field Acoustic Testing", http://ntrs.nasa.gov/archive/nasa/casi.ntrs.nasa.gov/20120007347_2012007750.pdf, Oct. 2010.
International Search Report and Written Opinion, International Application No. PCT/US2012/039787, dated Aug. 24, 2012.

*Primary Examiner* — John Chapman, Jr.
(74) *Attorney, Agent, or Firm* — Medler Ferro PLLC (57) ABSTRACT

A direct field acoustic testing system includes at least one control microphone, a controller operatively coupled to the control microphone such that the controller receives at least one input signal from the control microphone, and at least four acoustic transducers operatively coupled to the controller such that each transducer is separately controllable by the controller such that a separate output signal is received by each transducer from the controller. A setup is applied to each of the acoustical transducers. The acoustic output of each of the acoustical transducers is monitored using the at least one control microphone. The output signal of each control microphone with respect to each acoustical transducer is compared to a reference spectrum to create a matrix of error functions, and a corrected drive signal computed for each acoustical transducer is applied to the respective acoustical transducer.

28 Claims, 9 Drawing Sheets

Fig. 4A
MISO control, single acoustic output with 9 acoustic control inputs

Fig. 4B
MIMO control, 9 acoustic outputs and 9 acoustic control inputs

Fig. 5A – spectral variation
MISO Control, single acoustic output with 8 acoustic control inputs Fig. 5B – spectral variation
MIMO control, 12 acoustic outputs with 12 acoustic control inputs Fig. 6a
Coherence between 5 control points of a MISO system Fig. 6b
Coherence between 5 control points of a 12 x 12 MIMO system

DIRECT FIELD ACOUSTIC TESTING SYSTEM AND METHOD

BACKGROUND OF THE INVENTION

1. Field of the Invention

The present invention relates generally to the field of vibration testing of objects such as satellites, instrumentation or any other object whose reliability in operation may be evaluated using high intensity vibration testing. Specifically, the present invention relates to the use of direct field acoustic systems to perform vibration testing and to control means to allow direct field acoustic systems to closely approximate the properties of a reverberant field.

2. Background of the Invention

Many complex items such as satellites or other instruments are subjected to high levels of vibration, mechanical stress and other extreme conditions during operation or as part of the process of being placed into service. Failures may be difficult or impossible to repair after the object is placed in service and may be extremely costly. As a result there have been many techniques developed to evaluate the reliability of these objects during design, manufacture or certification to avoid in-service failures. Mechanical vibration testing is the most common form of test wherein the unit under test (UUT) is mounted to a vibratory platform driven by one or more types of mechanical transducers, such as hydraulic or electrodynamic. A vibration control system (VCS) is typically used to provide closed loop control of the test to achieve certain pre-specified test characteristics. Most mechanical testing is "Single-Axis" wherein a single group of commonly driven transducers is used to excite the UUT. However, a more complex control system involving multiple inputs and multiple outputs (MIMO) has also been used for the purpose of delivering specific test conditions to specific parts of the UUT. Such mechanical testing is limited to relatively low frequencies and is unsuitable for evaluating the impact of high intensity acoustic vibrational fields on the UUT.

Historically, the preferred method of evaluating the impact of high intensity acoustic fields has been through the use of a special reverberant high-energy acoustic chamber. These fixed installations use transducers driven by expanding gas to create very high acoustic levels. The reverberant nature of the chamber ensures a uniform but highly uncorrelated acoustic field which is considered necessary for many such tests. While these chambers are capable of very high acoustic levels, in excess of 150 db SPL, across a very broad acoustic bandwidth the acoustic field cannot be accurately controlled at higher frequencies, typically above 2 kHz, due to the nature of the transducers employed, and at low frequencies, typically below 50 Hz, where the low modal density of the chamber causes large spatial variations in the acoustic field. Since these are large fixed installations, very few of which exist, the UUT must typically be transported to the chamber. In the case of satellites, rockets and other such valuable objects transportation is costly, time consuming and risky. Additionally, the lack of control at high and low frequencies may result in over-testing and consequent damage to the UUT.

Accordingly, there has been interest in creating a system for acoustic testing which would offer accurate control of the test conditions across the entire spectrum of interest from approximately 20 Hz to 10 kHz and which could be temporarily assembled and configured on site thereby avoiding the risks of transporting the UUT. The first attempts to implement a so-called "Direct Field Acoustic Test" (DFAT) were carried out in the late 1990's using commercially available sound equipment to surround the UUT with a high intensity acoustic field. The usefulness of these tests was somewhat limited in that the acoustic field generated by the system exhibited substantial spatial variability and a high level of coherence meaning that it did not accurately simulate the desired reverberant field. In addition, the limitations of then available commercial sound equipment made it difficult to reliably achieve high intensity acoustic fields at the desired levels. In spite of these limitations commercial testing using DFAT systems began as early as 1998.

Thereafter, development work on DFAT systems continued. U.S. Pat. No. 6,484,580, issued November 2002 and assigned to Ball Aerospace & Technologies, Corp., incorporated by reference herein in its entirety, discloses the same system and method already in use along with a rudimentary control system based on $\frac{1}{3}^{rd}$ octave bands. Although no data on coherence is provided, there is no reason to believe that this system was any more successful in simulating a reverberant acoustic field than essentially identical systems previously used.

However, in October of 2003 a paper presented by Larkin and Smallwood at the Aero Space Test Seminar made important advances. Larkin and Smallwood recognized the importance of using fixed band-width narrow-band control for acoustic testing where the band-width of the control bands is a fixed frequency interval, for example a constant 3.125 Hz band-width, rather than a constant portion of an octave, for example, $1/n^{th}$ octave. They demonstrated that fixed band-width narrow-band control could reveal important acoustic response aberrations normally obscured by averaging over the commonly used $\frac{1}{3}^{rd}$ octave control bands. They disclosed how acoustic control inputs derived from microphones could be converted to narrow-band power spectral densities (PSD) which could in-turn be used as control inputs to a standard single output random VCS normally used for mechanical testing. They demonstrated that such an arrangement using fixed band-width narrow-band control could achieve stable closed loop control of an acoustic test system across the entire frequency range of interest from 20 Hz to 10 kHz. They further demonstrated that the system remained stable when using multiple control inputs to control a single output to the transducer array. This multiple-input-single-output control is known as a MISO control system. Application of these techniques to existing DFAT systems led to improved control capability and narrow-band spatial uniformity similar to the $\frac{1}{3}^{rd}$ octave average uniformity achieved by previous DFAT systems. Even with such improvements, these prior art DFAT systems failed to produce adequate spatial uniformity or low enough coherence to be considered a reliable predictor of results from true reverberant field testing.

In spite of these limitations direct field acoustic testing has seen increasing application due to its flexibility, convenience and the improving reliability of the test results. However, results must still be referenced to reverberant chamber results for absolute confidence. It would therefore be advantageous to provide a DFAT system capable of closely replicating the results of reverberant chamber testing.

SUMMARY OF THE INVENTION

Embodiments hereof include a direct field acoustic testing system with at least four groups of acoustical transducers driven by separately controllable drive signals disposed in appropriate locations so as to provide an acoustic field having a high degree of spatial uniformity and low spatial coherence.

Embodiments hereof also include a direct field acoustic testing system with at least one microphone disposed in an appropriate location to provide at least one acoustical input signal which is used to determine the separately controllable drive signals for the at least four groups of acoustical transducers which are disposed in appropriate locations so as to provide an acoustic field having a high degree of spatial uniformity and low spatial coherence.

Embodiments hereof also include a direct field acoustic testing system wherein acoustical signals from the at least one microphone are converted to a power spectral density using fixed band-widths no greater than 12.5 Hz for the purpose of providing more stable and accurate control of the at least four separately controllable drive signals.

Embodiments hereof also include a direct field acoustic testing system wherein acoustical signals from the at least one control microphone are converted to a form suitable for use as control inputs for an existing multiple-input-multiple-output (MIMO) mechanical vibration controller having at least one input and at least four separately controllable outputs. The separately controllable outputs of the MIMO mechanical vibration control system are converted to a form suitable for driving at least four separately driven groups of acoustical transducers, and specifications of the target acoustic field are converted to fixed band-width narrow-band power spectral densities for the purpose of providing stable closed or open loop control of an acoustical field having pre-specified characteristics.

Embodiments hereof also include providing acoustical monitoring means which is capable of inputting an acoustical signal into the control loop for the purpose of limiting the intensity of the acoustic field according to a set of pre-determined acoustical field specifications which have been converted to fixed band-width narrow-band power spectral densities.

BRIEF DESCRIPTION OF THE DRAWINGS

Embodiments of the invention will now be described, by way of example only, with reference to the accompanying schematic drawings in which corresponding reference symbols indicate corresponding parts.

DETAILED DESCRIPTION OF EMBODIMENTS OF THE INVENTION

Embodiments hereof are now described with reference to the figures where like reference characters/numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

Figure 1:
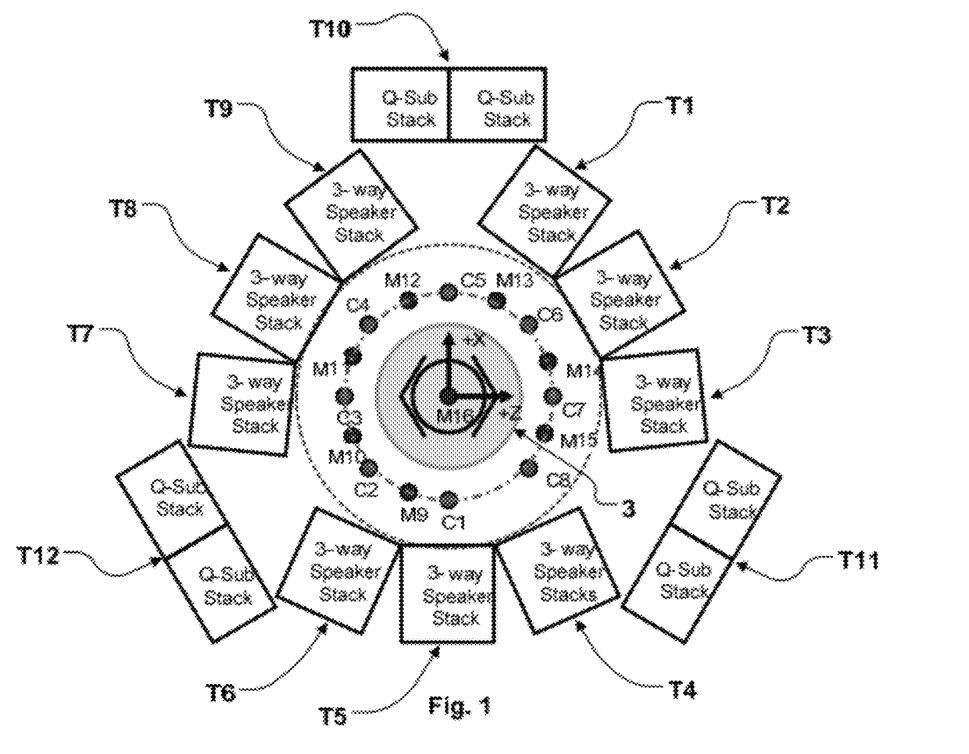
FIG. 1 schematic layout of an acoustical transducer group for direct field acoustic testing according to an embodiment hereof.

Referring to FIG. 1, an embodiment of a DFAT system includes a transducer array composed of electro-dynamic acoustic sources or transducers T1-T12 covering various frequency ranges arrayed around the unit-under test (UUT) 3 in a generally circular arrangement as shown. The transducer array in the embodiment shown is composed of twelve groups T1-T12 of eight transducers, of which nine groups T1-T9 are three-way electro-dynamic loudspeaker systems generally covering the frequency range above 100 Hz and three groups T10-T12 are electro-dynamic subwoofer loudspeakers generally covering the frequency range from 20 Hz to 200 Hz. In an non-limiting example, the three-way electro-dynamic loudspeaker systems of groups T1-T9 may each comprise two 15" drive units, two 8" drive units and three high frequency horns in a specially designed enclosure. In another non-limiting example, the electro-dynamic subwoofer loudspeakers of groups T10-T12 may each comprise a single 21" drive unit in a specially designed combination folded horn and bass-reflex enclosure. Control microphones C1-C8 are disposed at various positions around the UUT 3 for the purpose of providing information about the acoustic field to a control system (described below). As may be understood by those of ordinary skill in the art monitoring microphones M9-M16 may also be provided for monitoring the acoustic field at specific points of particular interest during operation but are not essential to the operation of this or any other embodiment hereof.

Figure 2:
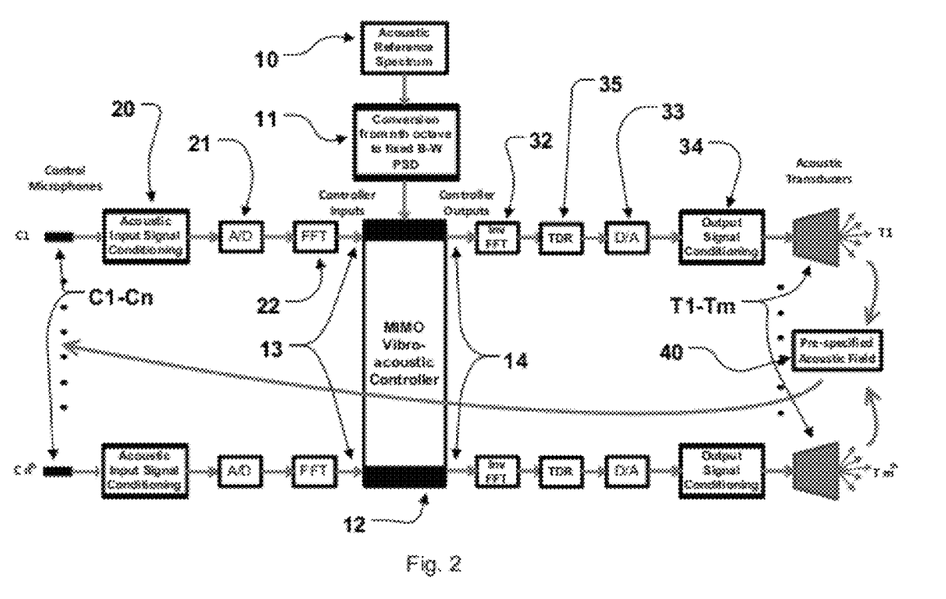
FIG. 2 is simplified block diagram of a direct field acoustic testing system according to an embodiment hereof.

Referring to FIG. 2, a simplified block diagram of DFAT system of FIG. 1 is shown. Each of the control microphones C1-Cn produces electrical signals which are representative of the acoustic field at each microphone. Each of the electrical signals is conditioned in an input signal conditioner 20 according to the input requirements of a vibro-acoustic controller 12. By way of example and not of limitation, conditioner 20 may include anti-aliasing or other filters, application of microphone calibration data referenced to appropriate standards, and scaling of the signal to represent the proper units. An analog to digital converter 21 converts the conditioned electrical signals to a digital format and the digitized signals are converted to fixed band-width narrow-band power spectral densities by application of a Fast Fourier Transform (FFT), as represented in block 22 of FIG. 2. Each of these resulting data streams is connected to one input 13 of the vibro-acoustic controller 12. Those of ordinary skill in the art recognize that the input signal conditioner 20, A/D converter 21, and the FFT 22 may be part of the controller 12. Each output 14 from the controller 12 is converted from a narrow-band power spectral density to a digitized time series by an inverse FFT, as represented in block 32. This digitized time series may then be time domain randomized 35 depending on the type of test being conducted and then converted to an analog signal in digital to analog converter 33. Each analog signal is then conditioned in output signal conditioner 34 according to the input requirements of the amplification and acoustic transducers T1-Tm. By way of example and not of limitation, the conditioning may include additional filtering, gain, attenuation or power amplification. Each of the conditioned signals is then applied to the respective acoustical transducer group, T1-Tm. A pre-specified acoustical reference spectrum 10 is converted from the standard 1/nth octave format to a fixed band-width narrow-band power spectral density format which is consistent with the format of the signals from the control microphones C1-Cn and applied to the vibro-acoustic controller inputs 13. Those of ordinary skill in the art recognize that the inverse FFT 32, time domain randomization, the digital to analog converted 33, and the output signal conditioner may part of the controller 12.

Figure 3:
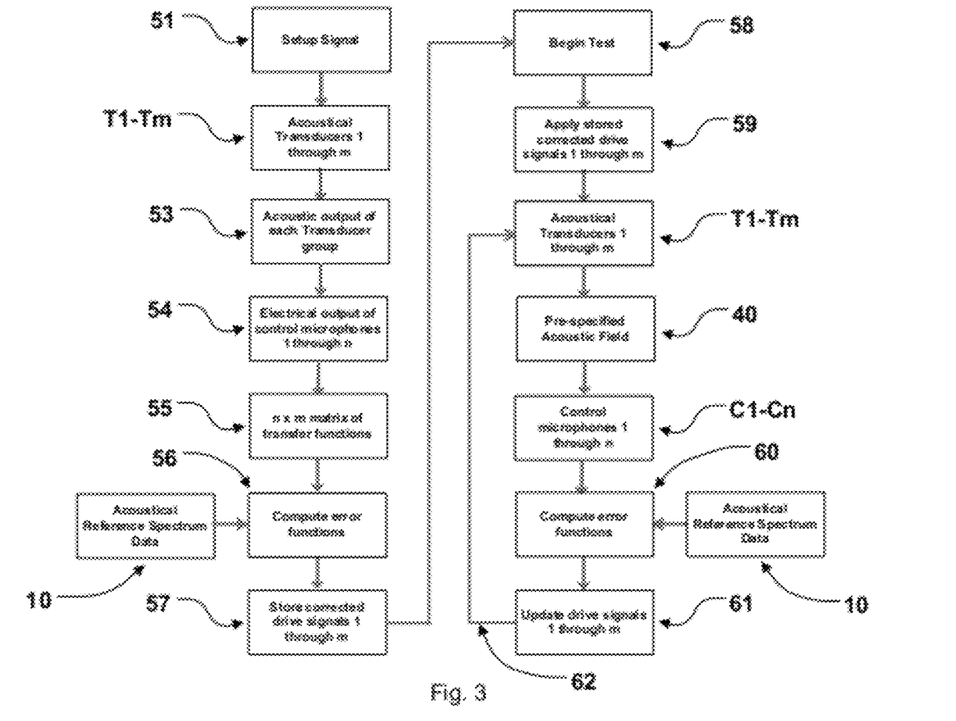
FIG. 3 is a simplified control diagram for the vibro-acoustic controller of the system of FIG. 2

The principles of multiple-input-multiple-output (MIMO) control logic will be familiar to those skilled in the art and may be applied in many different ways within the scope of the present invention in the implementation of this and other embodiments. Referring to FIG. 3, a simplified block diagram which describes generally the functioning of one possible embodiment of a MIMO vibro-acoustic controller 12 is shown. During the setup process a signal 51 is applied to each of the acoustical transducer groups T1-Tm. The acoustic output 53 of each transducer group is separately monitored by each control microphone C1-Cn. The electrical outputs of control microphones C1-Cn in response to each transducer group represent the transfer functions of each combination of transducer group and control microphone which are recorded in an n×m matrix 55 where each element is one such transfer function. These transfer functions are compared to the acoustical reference spectrum data 10. A matrix of error functions 56 is computed which is used to compute a corrected drive signal 57 for each of the transducer groups T1-Tm. At the start of the actual test 58 the previously stored 1 through m corrected drive signals 57 are applied 59 to the respective transducer groups T1-Tm. The resulting acoustic field is monitored by the control microphones C1-Cn and their outputs are compared to the acoustical reference spectrum data 10 from which error functions 60 are computed. These error functions 60 are used to provide real time updates of the drive signals 61 which are applied to through control loop 62 to the respective transducer groups T1-Tm. This embodiment may be operated in either closed loop control mode as shown in FIG. 3 or in open loop control mode. In open loop mode no real time adjustments to the drive signals are made after the initial application 59 of the stored corrected drive signals 57 computed during the setup process. Therefore the computation of error functions in block 60, the resulting update of drive signals 61 and feedback loop 62 would be omitted. Control microphones C1-Cn would therefore perform only a monitoring function.

Vibro-acoustic controller 12 may be any controller capable of performing the functions of the controller listed above. Controller 12 generally includes a processor and a graphical user interface (not shown), as known to those of ordinary skill in the art. In an embodiment, controller 12 may be an existing mechanical vibration controller such as, by way of example and not of limitation, the Spectral Dynamics Jaguar system.

In the embodiment shown and described with respect to FIGS. 1-3 there are n=8 control microphones C1-C8 and m=12 transducer groups T1-T12. However, those of ordinary skill in the art recognize that more or less control microphones and transducer groups may be utilized. For example, and not by way of limitation, the number of control microphones may be in the range of one to sixteen and the number of separately driven transducer groups may be in the range of four to sixteen. However, those of ordinary skill in the art recognize that additional control microphones and separately driven transducer groups may be utilized depending on the unit under test and the limits of controller 12. The band-width of the individual frequency bands of the power spectral density data used to represent the acoustical input signals and acoustical reference spectrum data is preferably equal to or less than 12.5 Hz and may be any suitable narrow band-width as determined by the characteristics of the available FFT functions such as and by way of example; 6.25 Hz, 3.125 Hz, 2.5 Hz, 1.25 Hz or 0.625 Hz.

Figure 4A:
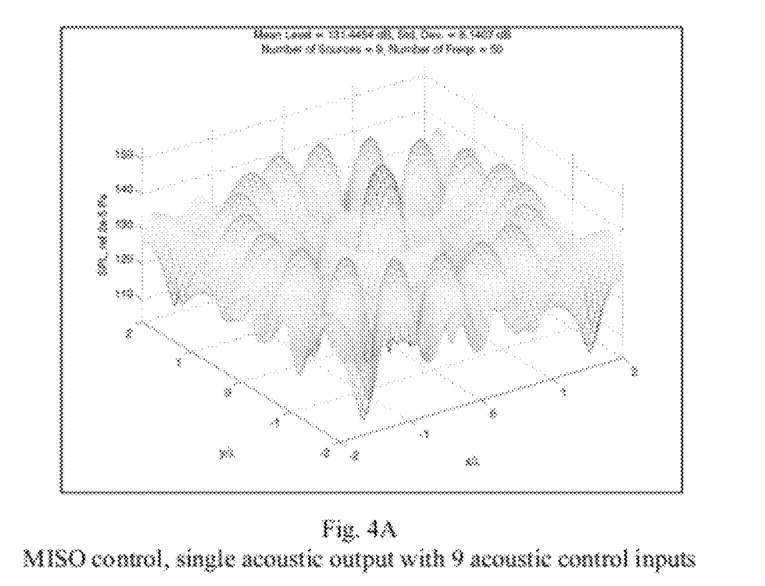
FIG. 4A is a diagram showing the spatial distribution of sound pressure from a simulated MISO acoustic field.
Figure 4B:
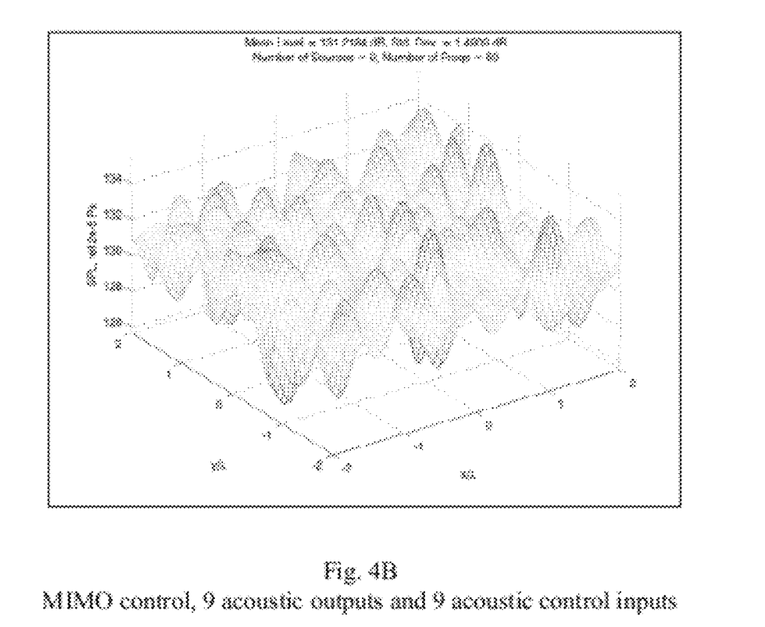
FIG. 4B is a diagram showing the spatial distribution of sound pressure from a simulated MIMO acoustic field.

Referring to FIG. 4A, there is shown a simulation of the spatial distribution of sound pressure from a prior art single-output direct field acoustic test system having nine acoustic sources/transducers driven from a single output. Referring now to FIG. 4B is shown a simulation of the spatial distribution of sound pressure from a DFAT system in accordance with an embodiment hereof employing nine separate outputs driving nine acoustic sources/transducers. As can be seen from inspection of the figures the spatial standard deviation of sound pressure achieved by the system shown in FIG. 4A is approximately 8 db, whereas the spatial standard deviation achieved by an embodiment hereof is approximately 1.5 db, as shown in FIG. 4B. Thus, improved spatial uniformity is shown which is well within the +/−6 db range frequently specified.

Figure 5A:
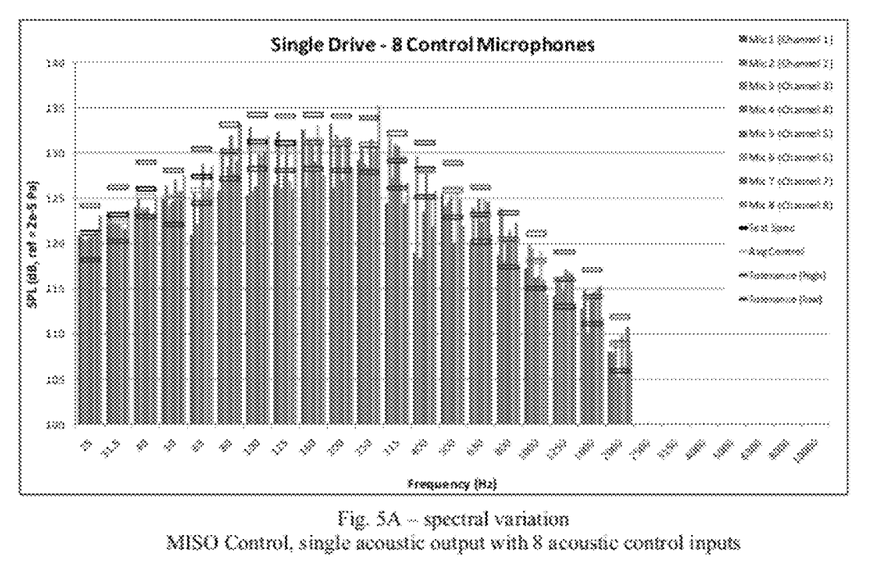
FIG. 5A is a diagram showing measured data for spectral variation at each control microphone position for a multiple-input-single-output (MISO) control with eight control microphones and a single output driving all acoustic transducers.
Figure 5B:
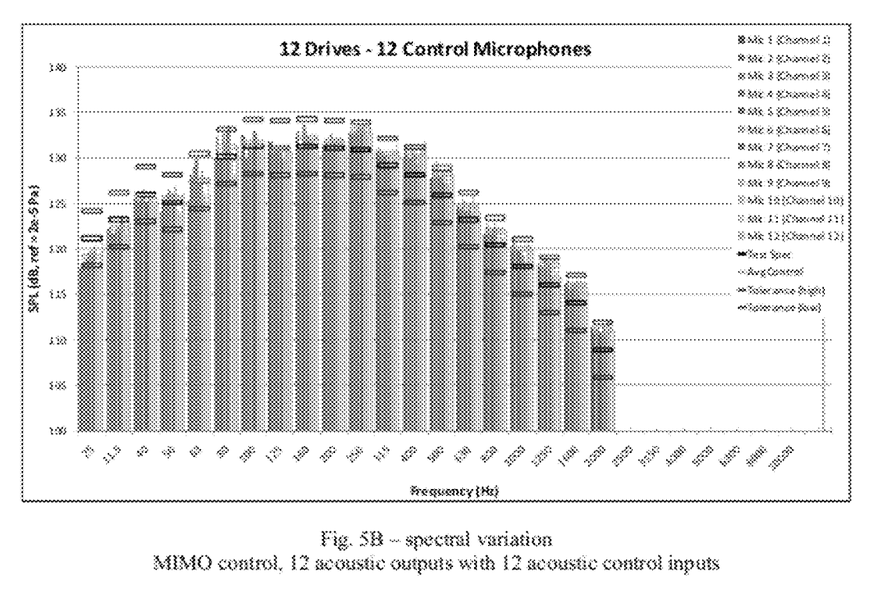
FIG. 5B is a diagram showing measured data for spectral variation at each control microphone position for a DFAT system according to an embodiment hereof having multiple-input-multiple-output (MIMO) control with twelve control microphones and twelve separate outputs driving twelve acoustic sources

Referring to FIG. 5A, there is shown actual measured data for spectral variation at each control microphone position for a prior art DFAT system employing multiple-input-single-output (MISO) control with eight control microphones and a single output driving all acoustic transducers. Referring to FIG. 5B, there is shown actual measured data for spectral variation at each control microphone position for a DFAT system in accordance with an embodiment hereof employing multiple-input-multiple-output (MIMO) control with twelve control microphones and twelve separate outputs driving twelve acoustic sources. Each figure shows the target magnitude in each band for the test represented by the center bar in addition to the maximum acceptable deviation of +/−6 db represented by the high and low bars in each band. As can be seen from inspection of the figures the system in accordance with an embodiment hereof, FIG. 5B, is able to maintain substantially all frequency bands within tolerance at all control microphone locations as compared to the system shown in FIG. 5A, which shows many out of tolerance bands at numerous control microphone locations.

Figure 6A:
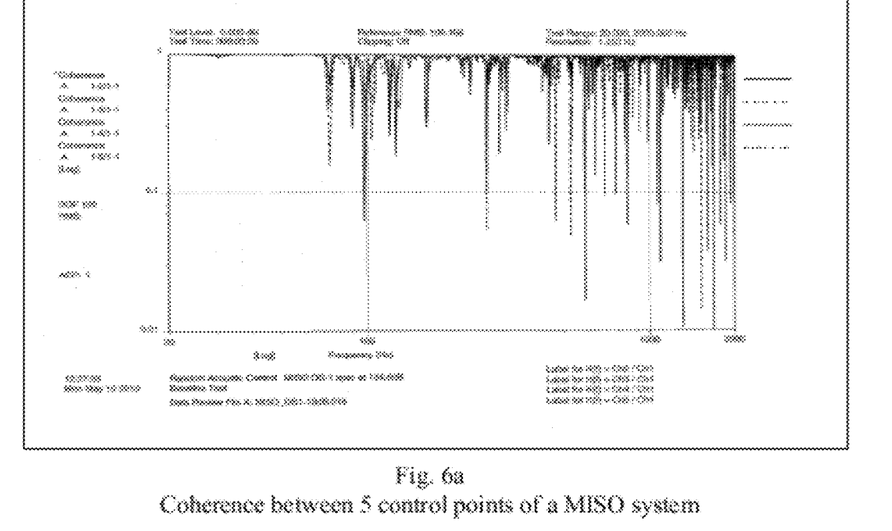
FIG. 6A is a diagram showing measured data for coherence between five control microphone locations for a prior art DFAT system employing MISO control.
Figure 6B:
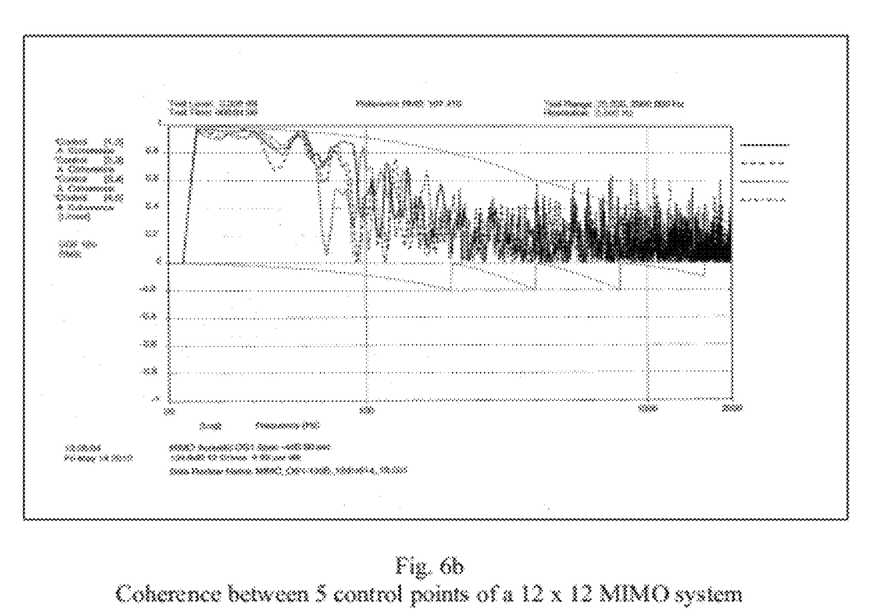
FIG. 6B is a diagram showing measured data for coherence between five control microphone locations for a DFAT system according to an embodiment hereof employing MIMO control with twelve control microphones and twelve separate outputs driving twelve acoustic sources.

Referring to FIG. 6A, there is shown actual measured data for coherence between five control microphone locations for a prior art DFAT system employing MISO control. In FIG. 6B, there is shown actual measured data for coherence between five control microphone locations for a DFAT system in accordance with an embodiment hereof employing MIMO control with twelve control microphones and twelve separate outputs driving twelve acoustic sources. As can be seen from inspection of the figures the system in accordance an embodiment hereof, FIG. 6B, achieves a low level of coherence substantially above 100 Hz, whereas the MISO system, FIG. 6A, displays a high level of coherence over most of the frequency range. In particular, the acoustic field created by an embodiment hereof, as shown in FIG. 6B, has an average coherence below 0.5 above 100 Hz, whereas the MISO system of FIG. 6A has an average coherence well above 0.5 over the entire range. Thus, the system of FIG. 6B creates a reverberant field, which is desirable for testing. The benefit of low coherence is that the acoustic field excites the surface of the UUT 3 randomly and avoids in-phase excitation over broad areas. In-phase excitation is much more likely to over-test and damage the UUT 3.

Figure 7:
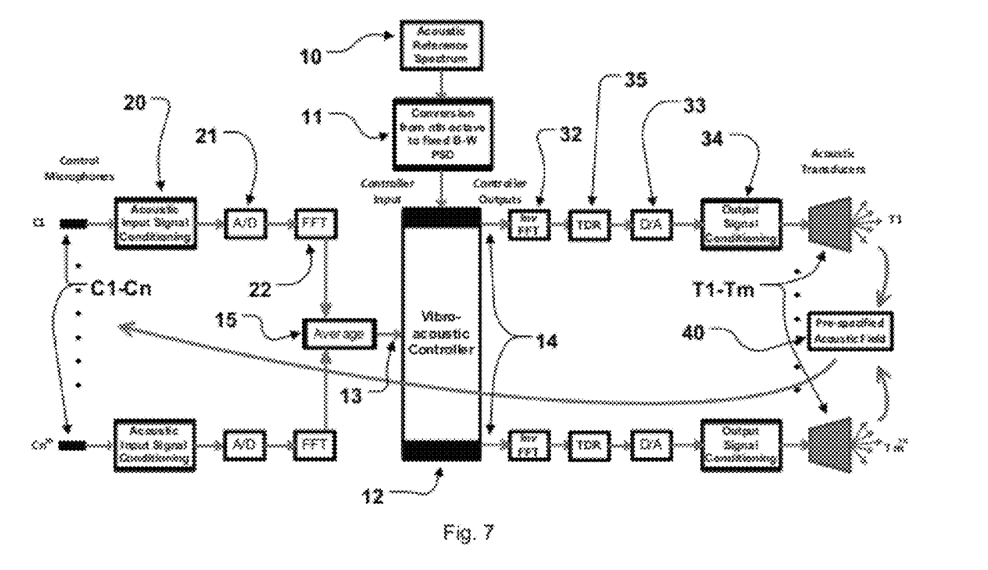
FIG. 7 is a simplified block diagram of a DFAT system according to an embodiment hereof utilizing averaged microphone outputs.

Referring to FIG. 7, a simplified block diagram of a DFAT system in accordance with another embodiment hereof is shown. For purposes of increasing the speed of the system to enable broader bandwidth operation it may be desirable to limit the number of control inputs. Acceptable reverberant field simulations may be achieved with a single input 13 which is the average 15 of a number of control microphones C1-Cn4. Any number of separately controllable outputs 14 may be applied to separately driven transducer groups T1-Tm. Preferably the number of separate outputs 14 and separately driven transducer groups T1-Tm is at least four and at least one control microphone C1 is used to create at least one average input signal 15. The remaining features shown in FIG. 7 are as described with respect to FIG. 2 and are marked with the same reference numerals.

Figure 8:
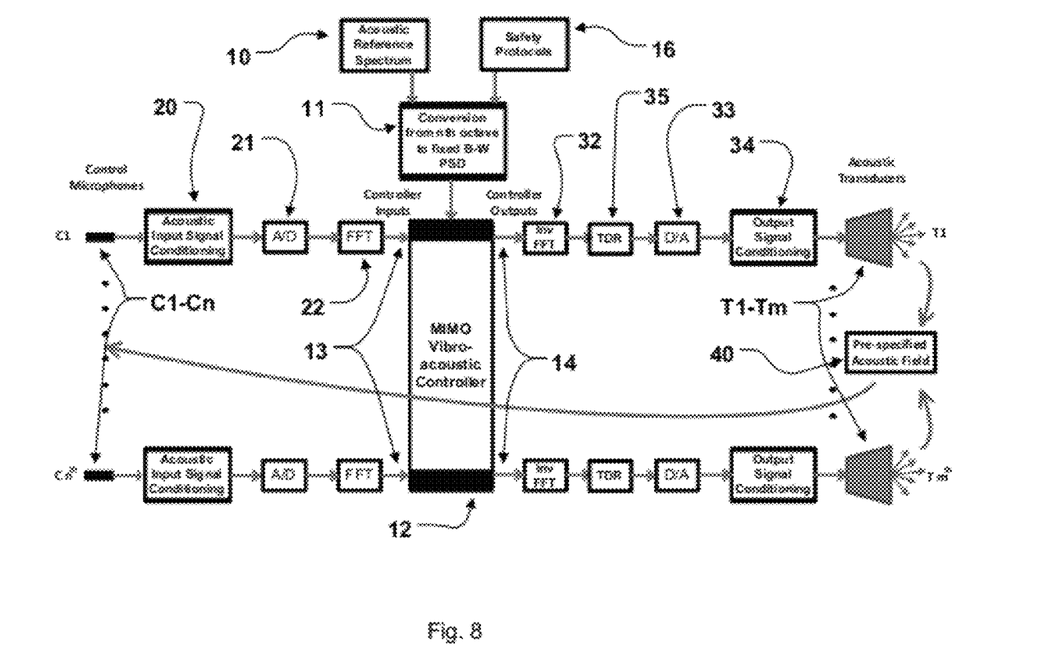
FIG. 8 is a simplified block diagram of a DFAT system according to an embodiment hereof with safety protocols

FIG. 8 is a simplified block diagram of a DFAT system in accordance with another embodiment hereof. In particular, FIG. 8 shows pre-specified safety protocols 16 supplied to the controller 12 in a fixed band-width narrow-band power spectral density format consistent with the controller inputs 13 and outputs 14. These safety protocols are provided for the purpose of aborting or limiting the test according to a pre-specified set of parameters. These parameters may include specifications for the protection of the UUT and also for the protection of the DFAT system itself. By way of example and not of limitation, such protocols may include a 6 db over test limit which will abort the test in the event that any control or monitoring location exceeds the test specification by more than 6 db in any frequency band. Similarly, a predetermined drive limit appropriate for the acoustical transducers, for example, 150 volts for each subwoofer, may be established. It is understood by those of ordinary skill in the art that the safety protocols described herein are not limited to the embodiment of FIG. 8 and may be applied to any of the embodiments disclosed herein. The remaining features shown in FIG. 8 are as described with respect to FIG. 2 and are marked with the same reference numerals.

Figure 9:
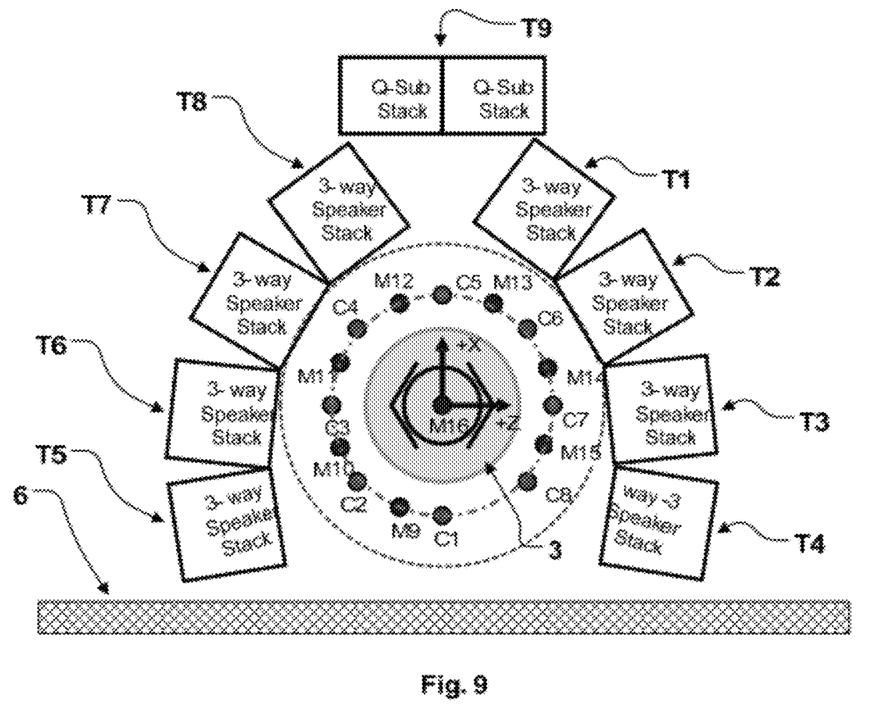
FIG. 9 is a schematic layout of an acoustical transducer group layout with reflective surfaces for direct field acoustic testing according to an embodiment hereof.

Referring to FIG. 9, another embodiment of an arrangement of acoustical transducer groups is shown. In some cases space or other considerations may prevent the use of a more or less circular arrangement such as shown in the embodiment of FIG. 1. In such cases and referring to FIG. 9, the UUT 3 may be disposed adjacent to an acoustically reflective surface or surfaces 6 such as a wall. Acoustical transducers T1-T9 may be arranged in the manner shown or any other manner which makes use of the reflective surface 6 or surfaces to help in the creation of a spatially uniform uncorrelated acoustic field with pre-specified characteristics around the UUT 3. Preferably the acoustical transducers will be distributed over at least a 180 degree angle as seen from the center of the UUT 3. The acoustical transducers may be also be arranged inside an enclosure and disposed in any manner relative to the UUT 3 that makes use of the acoustical properties of the enclosure to achieve an acoustic field with the desired pre-specified characteristics. The remaining features of the DFAT system of FIG. 9 are as described with respect to FIG. 1 and use the same reference numerals. Further, the control system described with respect to any of the embodiments herein may be utilized with the acoustical transducer group layout embodiment of FIG. 9.

It will be apparent to those of ordinary skill in the art that many more variations may be implemented which fall within the scope of the present invention. These may include by way of example and not of limitation; differing types or numbers of transducers, differing numbers of inputs and outputs, different transducer array layouts, alternate configuration or connection of transducer sub-arrays to said outputs, choices of locations for control or monitoring, any suitable type of multiple-input-multiple-output control system or logic, different types of or combinations signals for use during operation, or any other circumstances in which the disclosed multiple output techniques are applied to a direct field acoustic testing system.

What is claimed is:

1. A direct field acoustic testing system comprising:
a control microphone;
a controller operatively coupled to the control microphone such that the controller receives at least one input signal from the control microphone; and
at least four acoustic transducers operatively coupled to the controller such that the output of each transducer is separately controllable by the controller such that a separate output signal is received by each transducer from the controller,
wherein the controller is configured to compare an output signal of the control microphone with respect to each acoustical transducer to a reference spectrum to create a matrix of error functions, and
wherein the separate output signals received by each acoustic transducer are corrected drive signals computed from the matrix of error functions.

2. The direct field acoustic testing system of claim 1, wherein the control microphone comprises a plurality of control microphones, and wherein the input signal is an averaged signal from the plurality of control microphones.

3. The direct field acoustic testing system of claim 1, wherein the control microphone comprises a plurality of control microphones, and wherein the input signal comprises a separate input signal from each of the plurality of control microphones.

4. The direct field acoustic testing system of claim 1, wherein the control microphone and acoustic transducers are disposed adjacent a unit to be tested in a simulated reverberant field.

5. The direct field acoustic testing system of claim 4, further comprising an acoustic barrier disposed adjacent the unit under test.

6. The direct field acoustic testing system of claim 1, wherein the control microphone comprises at least four control microphones.

7. The direct field acoustic testing system of claim 1, wherein the controller is configured to convert an output signal of the control microphone to a fixed band-width narrow band spectral density.

8. The direct field acoustic testing system of claim 7, wherein the band-width of the fixed band-width narrow band spectral density is less than or equal to 12.5 Hz.

9. The direct field acoustic testing system of claim 1, wherein the reference spectrum is expressed as a fixed band-width narrow-band power spectral density.

10. The direct field acoustic testing system of claim 9, wherein the band-width of the fixed band-width narrow band spectral density is less than or equal to 12.5 Hz.

11. The direct field acoustic testing system of claim 1, wherein the output signals received by the acoustic transducers are configured to produce an acoustic field from the acoustic transducers with an average coherence below 0.5 above 100 Hz.

12. A method of direct field acoustic testing of a unit under test comprising the steps of:
positioning at least four acoustic transducers and at least one control microphone around the unit under test;
applying a setup signal to each of the acoustical transducers;
separately monitoring the acoustic output of each of the acoustical transducers using the at least one control microphone;
comparing an output signal of each control microphone with respect to each acoustical transducer to a reference spectrum to create a matrix of error functions;
computing a corrected drive signal for each acoustical transducer; and
applying each corrected drive signal to the respective acoustical transducer.

13. The method of claim 12, further comprising the steps of:
after applying the corrected drive signals to the acoustical transducers, monitoring the acoustic output of each of the acoustical transducers using the at least one control microphone;
comparing a second output of the at least one control microphone with respect to all of the acoustical transducers to the reference spectrum to create an updated matrix of error functions;
computing an updated corrected drive signal for each acoustical transducer; and
applying each updated corrected drive signal to the respective acoustical transducer.

14. The method of claim 12, wherein the output signal of the at least one control microphone is converted to a fixed band-width narrow band spectral density.

15. The method of claim 14, wherein the band-width of the fixed band-width narrow band spectral density is less than or equal to 12.5 Hz.

16. The method of claim 12, further comprising the steps of:
conditioning the output of each control microphone to create a conditioned signal;
converting the conditioned signal from analog to digital; and
converting the digitized signal to a fixed band-width narrow band spectral density.

17. The method of claim 16, wherein the band-width of the fixed band-width narrow band spectral density is less than or equal to 12.5 Hz.

18. The method of claim 16, wherein each corrected drive signal is converted from a narrow-band power spectral density to a digitized time series prior to being applied to the respective acoustic transducer.

19. The method of claim 12, wherein the reference spectrum is converted to a fixed band-width narrow-band power spectral density.

20. The method of claim 19, wherein the band-width of the fixed band-width narrow band spectral density is less than or equal to 12.5 Hz.

21. A direct field acoustic testing system comprising:
a plurality of control microphones;
a controller operatively coupled to the control microphones such that the controller receives at least one input signal from the control microphones; and
at least four acoustic transducers operatively coupled to the controller such that each transducer receives a different output signal from the controller,
wherein the controller is configured to compare an output signal of each control microphone with respect to each acoustical transducer to a reference spectrum to create a matrix of error functions, and
wherein the output signal received by each acoustic transducer is a corrected drive signal computed from the matrix of error functions.

22. The direct field acoustic testing system of claim 21 wherein the controller is configured to update in real time the signals received by each acoustic transducer during operation.

23. The direct field acoustic testing system of claim 21, wherein the system is configured to average signals from the plurality of control microphones such that the at least one input signal is an averaged signal from the plurality of control microphones.

24. The direct field acoustic testing system of claim 21, wherein the input signal comprises a separate input signal from each of the plurality of control microphones.

25. The direct field acoustic testing system of claim 21, wherein the controller is configured to convert output signals of the control microphone to a fixed band-width narrow band spectral density.

26. The direct field acoustic testing system of claim 25, wherein the band-width of the fixed band-width narrow band spectral density is less than or equal to 12.5 Hz.

27. The direct field acoustic testing system of claim 21, wherein the reference spectrum is expressed as a fixed band-width narrow-band power spectral density.

28. The direct field acoustic testing system of claim 27, wherein the band-width of the fixed band-width narrow band spectral density is less than or equal to 12.5 Hz.

* * * * *